United States Patent
Kojima et al.

(10) Patent No.: US 6,169,219 B1
(45) Date of Patent: Jan. 2, 2001

(54) ALKYLATION OF AROMATICS WITH REMOVAL OF POLYMERIC BYPRODUCTS

(75) Inventors: Masami Kojima, Arlington, VA (US); Thomas R. Fritsch, Villa Park; Kurt A. Detrick, Glen Ellyn, both of IL (US)

(73) Assignee: UOP LLC, Des Plaines, IL (US)

( * ) Notice: Under 35 U.S.C. 154(b), the term of this patent shall be extended for 0 days.

(21) Appl. No.: 09/328,839

(22) Filed: Jun. 9, 1999

Related U.S. Application Data

(60) Provisional application No. 60/088,676, filed on Jun. 9, 1998.

(51) Int. Cl.$^7$ .......................... C07C 2/64; C07C 15/107; C07C 2/66; C07C 2/68
(52) U.S. Cl. .......................... 585/449; 585/455; 585/456; 585/468
(58) Field of Search ................................ 585/449, 455, 585/456, 468

(56) References Cited

U.S. PATENT DOCUMENTS

| | | | |
|---|---|---|---|
| 3,474,154 | * 10/1969 | Yamanaka et al. | 260/671 |
| 3,484,498 | 12/1969 | Berg | 260/671 |
| 3,494,971 | 2/1970 | Fenske | 260/671 |
| 4,523,048 | 6/1985 | Vora | 585/323 |
| 5,012,021 | 4/1991 | Vora et al. | 585/315 |
| 5,196,574 | * 3/1993 | Kocal | 562/94 |
| 5,276,231 | 1/1994 | Kocal et al. | 585/323 |

OTHER PUBLICATIONS

Dr. Herman S. Bloch UOP Discloses New Way to Make Linear Alkylbenzene.,*The Oil and Gas Journal* (Jan. 16, 1967) pp. 79–81.

*Ullmann's Encyclopedia of Industrial Chemistry*,volumes A8 and A13, 5$^{th}$ Ed., VCH (Weinheim, Germany) pp. 338–343. ISBN 3–527–20108–4 (Weinheim); ISBN 0–89573–158–4 ( New York).

Harold U. Hammershaimb et al. "Alkylation" in *Kirk–Othmer Encyclopedia of Chemical Technology*, 4$^{th}$ Ed. (John Wiley and Sons, New York, 1992) pp. 85–112. ISBN 0–471–52669–X TP9.E685.

D.R. Taylor and D.B. Jenkins "Acid–Activated Clays" *Transactions, Society of Mining Engineers of AIME*, vol. 282, pp. 1901–1910.

W.L. Haden, Jr. And I.A. Schwint "Attapulgite: Its Properties and Applications" *Industrial and Engineering Chemisty*, vol. 59, No. 9, Sep. 1967, pp. 58–59.

R.C. Berg et al. "Detergent Alkylate" *Encyclopedia of Chemical Processing and Design*, (Marcel Dekker, Inc., New York, 1982) vol. 15, pp. 266–284 ISBN 0–8247–2451–8 (v.1) TP9.E66.

Royston M. Roberts and Ali Ali Khalaf Friedel–Crafts Alkylation Chemistry: *A Century of Discovery* (New York, Marcel Dekker, Inc., 1984) pp. 701–726.

*Handbook of Petroleum Refining Processes* Edited by : Robert A. Meyers (New York, McGraw–Hill, 2$^{nd}$ Edition 1997) pp. 1.53–1.66 and pp. 5.11–5.19 ISBN 0–07–041796 2 TP690.H34.

Sales Bulletin: "High Purity Aromatics" Süd–Chemie AG Apr. 1993 (Address: Süd–Chemie AG, Sparte Katalysatoren, Postfach 20 22 40, D–8000 München 2).

* cited by examiner

*Primary Examiner*—Marian C. Knode
*Assistant Examiner*—Thuan D. Dang
(74) *Attorney, Agent, or Firm*—John G. Tolomei; Michael A. Moore

(57) ABSTRACT

Detergent-quality linear alkylaromatics are recovered from an alkylation reactor effluent containing polymeric byproducts, such as dimers and trimers of the olefinic feedstock. The effluent stream passes to another reactor operating at a higher temperature than the first reactor. Heavy alkylate is separated from the detergent-quality linear alkylaromatics by conventional separation methods such as distillation. This invention decreases the concentration of polymeric byproducts in the linear alkylaromatics. The benefits of this invention include a higher linearity and/or a lower bromine index in the detergent-quality linear alkylaromatic product, as well as a lower color after sulfonation of the linear alkylbenzene sulfonate.

27 Claims, No Drawings

ALKYLATION OF AROMATICS WITH REMOVAL OF POLYMERIC BYPRODUCTS

CROSS-REFERENCE TO RELATED APPLICATION

This application claims the benefit of U.S. Provisional Application No. 60/088,676, filed Jun. 9, 1998.

FIELD OF THE INVENTION

The field of the invention is the production of alkylated aromatic compounds.

BACKGROUND OF THE INVENTION

About thirty years ago, it became apparent that household laundry detergents made of branched alkylbenzene sulfonates were gradually polluting rivers and lakes. Solution of the problem led to the manufacture of detergents made of linear alkylbenzene sulfonates (LABS), which were found to biodegrade more rapidly than the branched variety. Today, detergents made of LABS are manufactured world-wide.

LABS are manufactured from linear alkyl benzenes (LAB). The petrochemical industry produces LAB by dehydrogenating linear paraffins to linear olefins and then alkylating benzene with the linear olefins in the presence of HF. This is the industry's most common process. Over the last decade, environmental concerns over HF have increased, leading to a search for substitute processes employing catalyst other than HF that are equivalent or superior to the standard process. Six of the chief criteria for a substitute process are: extent of conversion, linearity of alkylbenzenes, monoalkylbenzene selectivity, linear monoalkylbenzene selectivity, bromine index of alkylbenzenes, and color of the alkylbenzene sulfonates. At this point the definition of several terms are necessary to adequately understand and appreciate what follows.

i. Linearity.

The reaction of linear olefins with benzene in principle proceeds according to the equation, $$C_6H_6 + R_1CH\!=\!CHR_2 \rightarrow C_6H_5CH(R_1)CH_2R_2 \text{ or } C_6H_5CH(R_2)CH_2R_1.$$

Note that the side chain is branched solely at the benzylic carbon and contains only one branch in the chain. Although strictly speaking this is not a linear alkylbenzene, nonetheless the terminology which has grown up around the process and product in fact includes as linear alkylbenzenes those materials whose alkyl group chemically arises directly from linear olefins and therefore includes alpha-branched olefins. Because alkylation catalysts may also induce the rearrangement of olefins to give products which are not readily biodegradable, for example, alpha, alpha-disubstituted olefins which subsequently react with benzene to afford an alkyl benzene with branching at other than the benzylic carbon,

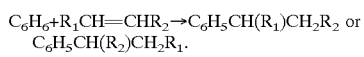

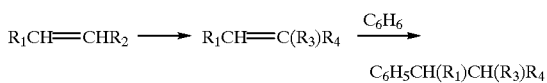

the degree to which the catalyst effects formation of linear alkyl benzenes (LAB) is another important catalyst parameter. The degree of linearity can be expressed by the equation, $$D = L/M*100,$$

where D equals degree of linearity, L equals moles of linear monoalkyl benzene produced, and M equals moles of monoalkyl benzene produced.

ii. Alkylation conversion.

In alkylation, benzene typically is supplied in excess and therefore conversion is defined in terms of the olefin. The degree of conversion at a constant ratio of excess benzene relative to olefin and a constant temperature is a measure of a catalyst's activity in a process. The degree of conversion may be expressed by the formula, $$V = C/T*100,$$

where V equals percent conversion, C equals moles of olefin consumed, and T equals moles olefin initially present.

iii. Monoalkylbenzene selectivity

Monoalkylbenzene selectivity is defined as the percentage of total olefin consumed under reaction conditions which appears as monoalkylbenzene and can be expressed by the equation, $$S = (M/C) \times 100,$$

where S equals monoalkylbenzene selectivity, M equals moles of monoalkylbenzenes produced, and C equals moles olefin consumed. The higher the monoalkylbenzene selectivity, the more desirable is the process. An approximate measure of monoalkylbenzene selectivity is given by the equation, $$S = \frac{\text{weight monoalkylbenzene}}{\text{weight total products}} \times 100$$

where "total products" includes monoalkylbenzenes, polyalkylbenzenes, and olefin oligomers. At high selectivity (S>85%) the results calculated from the two equations are nearly identical. The after of the foregoing two equations is routinely used in commercial practice because of the difficulty in distinguishing between oligomers and polyalkylbenzenes.

iv. Linear monoalkylbenzene selectivity

Linear monoalkylbenzene selectivity is defined as the percentage of total olefin consumed under reaction conditions which appears as linear monoalkylbenzene and can be expressed by the equation, $$R = (L/C) \times 100,$$

where R equals linear monoalkylbenzene selectivity, L equals moles of linear monoalkylbenzenes produced, and C equals moles olefin consumed. The higher the linear monoalkylbenzene selectivity, the more desirable is the process. Linear monoalkylbenzene selectivity is related to linearity and monoalkylbenzene lo selectivity by the equation, $$R = (D \times S) \times 100.$$

v. Bromine index

When an olefin alkylates benzene, the primary product is an alkyl benzene with a side chain having no points of unsaturation. However, byproducts may also form as a result of an olefin oligomerizing with another olefin, such as by the reaction,

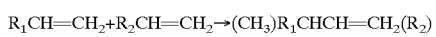

In addition to dimers, trimers and tetramers may also form. All of the resultant oligomers are olefinic, as are the products of cracking an oligomer. Cracking can occur by one of several reactions and can produce not only monoolefins but also diolefins, such as by the reaction,

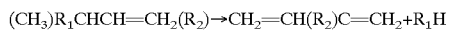

Thus, the oligomers can, but need not, contain a number of carbon atoms that is a multiple of the number of carbon atoms in the feed olefin. Regardless of the exact nature of the oligomers formed, a useful indication of the extent to which oligomers as opposed to alkyl benzenes are byproducts of the alkylation reaction is the product bromine index.

A standard test for bromine index is UOP Method 304-90, "Bromine Number and Bromine Index of Hydrocarbons by Potentiometric Titraition," for which information is available from UOP LLC, 25 E. Algonquin Rd., Des Plaines, Ill. 60017, USA. It should be pointed out that there are at least three other standard test methods for bromine index, including ASTM D 1492, "Bromine Index of Aromatic Hydrocarbons by Coulometric Titration;" ASTM D 5776, "Bromine Index of Aromatic Hydrocarbons by Electrometric Titration;" and ASTM D 2710, "Bromine Index of Petroleum Hydrocarbons by Electrometric Titration." Information on ASTM methods is available from American Society for Testing and Materials (ASTM), 100 Barr Harbor Drive, West Conshohocken, Pa., USA. UOP Method 304-90 is not equivalent, to each of these or other methods of determining bromine index, and therefore it is to be understood that, in the context of measuring bromine index when practicing this invention, only UOP Method 304-90 is to be used for measuring the bromine index. Accordingly, as used hereinafter, the term "bromine index" means bromine index as determined by UOP Method 304-90.

It is useful, when analyzing detergent alkylation streams for bromine index, to report the bromine index on a basis that is not dependent on the feed aromatic (e.g., benzene) content or the paraffin content of the stream. In the case of the feed aromatic, this is because the feed aromatic is usually provided in a molar excess to the feed olefin and this molar excess can vary over a relatively wide range, depending on the particular alkylation catalyst, the desired alkylation catalyst life, etc. The concentration of paraffins, which are generally unreactive at alkylation conditions, can similarly vary widely, depending of the source and nature of the olefinic feedstock. In order to determine the bromine index of a stream on a feed-aromatic-free and paraffin-free basis, a sample of the stream is distilled to remove the feed aromatic (e.g., benzene) Then, an aliquot position of the feed-aromatic-free remainder of the sample is analyzed according to UOP Method 304-90. An aliquot portion of the feed-aromatic-free remainder is a portion of the feed-aromatic-free remainder that has essentially the same composition as the feed-aromatic-free remainder. Next, another aliquot portion of the feed-aromatic-free remainder is analyzed by gas chromatography for paraffin content. Next, using the results of the gas chromatography, a weight ratio is computed according to the following formula:

$$1/(1-x),$$

where x is the mass fraction of the stream that consists of paraffins. Finally, the bromine index on a feed-aromatic-free and paraffin-free basis is computed by multiplying the measured bromine index by the weight ratio.

vi. Post-sulfonation color.

An aesthetically important property of LABS is color, and colorless LABS is preferred. The color of LABS made by sulfonating a mixture containing LAB and byproducts of the LAB production depends on the particular sulfonation method, on the concentration of the LAB and the byproducts in the mixture, and on whether the other components are either color bodies or color body precursors that is become color bodies on sulfonation. For a given sulfonation method, sulfonation of LAB produces LABS having relatively little color, but sulfonation of olefins, oligomers, and other byproducts produces sulfonated species having relatively more color, usually shades of yellow or brown. Suitable standard test methods for measuring color after sulfonation include the Klett color index method, in which a blue light (wavelength 420–430 nm) passes through a solution of the product LABS, a spectrophotometer measures the extinction (log $l_o/l$) of the blue light, and the extinction is multiplied by 1000 to provide the index. Another suitable test method is ASTM D 1209, "Color of Clear Liquids (Platinum-Cobalt Scale)," for which information is available from ASTM. This test method is similar to that recorded in the Standard Methods for the Examination of Water and Waste Water of the American Public Health Association and is often referred to as "APHA color." In this method, the absorbance of the product LABS at a particular wavelength using a spectrophotometer, and the absorbance is proportional to color formation in the product LABS. As explained in ASTM D 1209, the petroleum industry uses ASTM D 156, "Saybolt Color of Petroleum Products (Saybolt Chromometer Method)" for measuring the color of hydrocarbon solvents, but Saybolt color is not commonly used outside of the petroleum industry and moreover exact equivalencies between APHA color and Saybolt color are difficult to obtain.

Consequently, the ideal process is one where V equals 100, S equals 100, D equals 100, R equals 100, bromine index of the total alkylation reactor effluent on a benzene-free and paraffin-free basis is zero, and the LAB post-sulfonation is colorless. The minimum requirement is that linearity be at least 90% at a selectivity of at least 85% and at a conversion of at least 99%, with a bromine index on a benzene-free and paraffin-free basis of less than 500. These are minimum requirements; that is, if a process fails to meet all of the foregoing requirements simultaneously the process is commercially unacceptable.

Of these criteria, linearity is assuming added importance and significance in view of the expectation in some areas that the minimum standard for linearity in detergents will be 92–95% near term, increasing to 95–98% by about the year 2005. Bromine index of LAB-containing detergent alkylation effluents prior to sulfonation is also assuming increased importance and significance as a broad and yet practical indicator of the overall quality and suitability of a detergent alkylation effluent for use in detergent manufacture. Because bromine index detects olefinic components, a low bromine index of the detergent alkylation effluent indicates high alkylation conversion of olefins as well as high alkylation selectivity to alkylaromatics as opposed to olefinic oligomers. In addition, a low bromine index is a harbinger of low post-sulfonation color because olefinic components tend to be color body precursors on sulfonation. Consequently, the ideal process is one in which the bromine index of the detergent is zero.

One of the causes for low linearity is rearrangement of linear olefins induced by the alkylation catalyst, as previously mentioned. In general terms, olefin rearrangement includes double bond migration, cis-trans isomerization, and skeletal rearrangement, but LAB producers are chiefly concerned with skeletal rearrangement because double bond migration and cis-trans isomerization do not degrade a linear olefin into a nonlinear (i.e., branched) olefin. Skeletal rearrangement equilibria are dependent on temperature, with a decrease in temperature tending to favor nonlinear olefins over linear olefins. For a given alkylation catalyst, skeletal rearrangement kinetics are temperature-dependent, with a decrease in temperature tending to lower the rate of rearrangement from linear to nonlinear olefins. In commercial LAB production, the economical balance between these conflicting tendencies has been struck in favor of operating alkylation reactors at relatively low temperatures in order to minimize the rate at which rearrangement allows nonlinear concentrations to approach equilibrium.

Another cause for poor linearity of detergent alkylate is alkyl benzene rearrangement, that is rearrangements of the linear alkyl group of the LAB after the alkyl group has become attached to the benzene ring. A discussion of these rearrangements in the context of linear $C_4$-alkyl benzenes and linear $C_5$-alkyl benzenes is found in Chapter 8 of the book entitled *Friedel-Crafts Alkylation Chemistry: A Century of Discovery*, by R. M. Roberts and A. A. Khalaf, published by Marcel Dekker, Inc., New York, 1984. However, it is generally believed that these rearrangements occur to alkyl benzenes that have linear $C_5$-alkyl groups to $C_{25}$-alkyl groups as well, including LAB for detergents. The equilibria for these alkyl benzene rearrangements are similar to that for olefinic skeletal rearrangements, with a decrease in temperature tending to favor nonlinear alkyl groups over linear alkyl groups. From a kinetic viewpoint, higher temperature tends to accelerate the rate of rearrangement of a linear alkyl group to a nonlinear alkyl group. Thus, as in the case of olefin skeletal rearrangement, not only is it necessary to trade off the relative advantages of equilibria and kinetics but generally concerns regarding kinetics dominate, so that minimizing the rate of alkyl benzene rearrangement is another reason why commercial LAB processes tend to operate at relatively low temperatures.

One of the causes for high bromine index is oligomerization of the olefinic alkylating agent. Commercial LAB processes, in an attempt to minimize oligomerization in the alkylation reactor, generally operate at relatively low reactor temperatures because low temperatures slow the oligomerization rate, even though oligomerization equilibria generally favor the formation of oligomers at low temperature. Accordingly, commercial practice has been to operate at relatively low temperatures in order to minimize the rates of both olefin skeletal rearrangement and olefin oligomerization.

For all of the above reasons, LAB alkylation processes tend to operate at relatively low temperatures. However, these relatively low temperatures decrease the rates not only of skeletal rearrangement and oligomerization, but also of alkylation itself. Relatively low temperatures thus also mean relatively low conversion of olefin to the desired detergent alkylate. Thus, commercial operators of LAB processes face a dilemma: operate at low temperature to minimize olefinic skeletal rearrangement, alkyl benzene rearrangement, and olefin oligomerization, or else operate at high temperature to maximize olefin conversion. Commercially, in producing LAB on an industrial scale, choosing to operate at a relatively low alkylation temperature incurs additional capital and/or operating costs. A commercial operator must either invest more capital for larger reactors and/or more alkylation catalyst or else spend more in operating costs for separating LAB from unconverted olefins and benzene and for recycling these unconverted feed stocks to the alkylation reactor.

One approach that has been used in commercial LAB processes to decrease the bromine index of the LAB is to pass the alkylation reactor effluent to a conventional product recovery facility, such as those shown in FIGS. 1.5.2 and 1.5.3 on pages 1.57 and 1.58 of the book edited by R. A. Meyers entitled *Handbook of Petroleum Refining Processes*, published by The McGraw-Hill Companies (New York, 1997). Such facilities remove benzene, paraffins, and heavy alkylate and produce a product LAB stream. Then, to reduce the bromine index, the product LAB stream is contacted with a fixed bed of clay. Typical clays include montmorillonite and bentonite. Although clay treating does decrease the bromine index of the product LAB stream, the clay gradually becomes ineffective at decreasing the bromine index and must be replaced. Consequently, the disadvantage of this approach are the costs for purchasing and loading fresh clay and for unloading and disposing of spent clay.

Accordingly, processes are sought for producing alkyl aromatic hydrocarbons, particularly LAB, which avoid this dilemma and produce LAB that has high linearity and low bromine index.

SUMMARY OF THE INVENTION

This invention is a process for producing alkylaromatics having high linearity and low bromine index for use in producing detergents. The process alkylates aromatics with linear olefins using two alkylation zones in series, where the first zone operates at conditions that maximize linearity and the second zone operates at conditions that minimize bromine index. In this invention, the first alkylation zone operates at relatively low temperatures such that the linear olefins tend to alkylate the aromatics without first isomerizing to non-linear (i.e., branched) olefins. Thus, in comparison to an alkylation zone that operates at a higher temperature and produces fewer linear alkylaromatics, the first alkylation zone of this invention produces more linear alkylaromatics. In addition to linear alkylaromatics, however, polymeric byproducts are also formed in the first alkylation zone. These polymeric byproducts generally have boiling points that are sufficiently close to those of the desired linear alkylaromatics that they cannot be readily separated from the linear alkylaromatics using distillation. Moreover, some of these polymeric byproducts are olefins, which, if left in the first alkylation zone effluent would raise the bromine index of the product distillate fraction containing the linear alkylaromatics to such an extent that fraction would not be a suitable detergent feedstock. Accordingly, this invention passes the first alkylation zone effluent to a second alkylation zone which operates at a relatively higher temperature than the first alkylation zone. One of the benefits of this invention is a decrease in the bromine index of the linear alkylaromatics. Without being limited to any particular theory, it is believed that in the second alkylation zone, the polymeric byproducts alkylate aromatics to produce heavy alkylate, which can be readily separated from the desired linear alkylaromatics by distillation. Accordingly, the linear alkylaromatics that are recovered from the effluent of the second alkylation zone have both high linearity and a low bromine index.

The basis for this invention is the surprising observation that, at relatively high temperature conditions that are suitable for alkylating aromatics with linear olefins in the presence of a solid alkylation catalyst, linear olefins are readily isomerized to non-linear (i.e., branched) olefins but linear alkylaromatics are relatively resistant to isomerization to non-linear alkylbenzenes. This observation was surprising because persons of ordinary skill in the art of detergent alkylation had expected that any operating conditions that are sufficient to isomerize linear olefins would likewise be sufficient to isomerize the linear alkyl groups of linear alkylaromatics. For this reason, prior processes for producing detergent alkylate did not operate at conditions, such as relatively high temperatures, which isomerized linear olefins, because persons of ordinary skill in the art believed that the result would be the production of more non-linear aromatics, whether by alkylating aromatics with non-linear olefins, or by isomerizing linear alkylaromatics to nonlinear alkylaromatics, or by both routes. Upon sulfonation such non-linear alkylaromatics would, of course, have poor biodegradability characteristics.

It has now been discovered that solid catalyst detergent alkylation processes can produce alkylaromatics having high linearity and low bromine index while operating at conditions that would normally isomerize linear olefins to non-linear olefins. It has now been found that, if the linear olefins alkylate the aromatics and produce linear alkylaromatics at conditions that do not isomerize the linear olefins, then the linear alkylaromatics can be exposed to conditions that would normally isomerize the linear olefins without any significant isomerization of the linear alkylaromatics to non-linear alkylaromatics. Thus, this invention effects a certain minimum degree of conversion, that is alkylation of the airomatics with the linear olefins, prior to exposing to conditions that could isomerize the olefins. The fewer the olefins that are exposed to olefin-isomerizing conditions, the fewer are the olefins that isomerize, and the less will be the production of non-linear alkylaromatics. The linear alkylaromatics are not degraded to non-biodegradable non-linear alkylaromatics by exposure to conditions that would normally isomerize the linear olefins.

In addition to having a high linearity, the linear alkylaromatics fraction produced according to the method of this invention also has a low bromine index. It is believed that the reduction in bromine index primarily occurs because polymeric byproducts, which are generally formed to some extent by oligomerization at the alkylation conditions, readily alkylate aromatics at the conditions that would normally isomerize the linear olefins to produce heavy alkylate. That is, the conditions that are optimal for alkylating aromatics with the polymeric byproducts are the same conditions that are optimal for isomerizing the linear olefins, and it is for this reason that the prior art processes did not operate at these conditions.

Thus, the prior art processes were faced with the dilemma of either operating at low temperature in order to maximize linearity or operating at high temperature in order to minimize bromine index. This invention avoids this dilemma by using a two-step reaction process. First, this invention operates at low temperature when substantial amounts of linear olefins are unreacted, that is when the possibility of producing non-linear alkylaromatics by isomerizing these to non-linear olefins is the greatest. Second, this invention operates at high temperature when most of the olefins have already reacted, that is when the possibility of isomerizing them to non-linear olefins is relatively small and the possibility of isomerizing linear alkylaromatics to non-linear alkylaromatics is relatively small.

A primary objective of this invention is to produce alkylaromatics. Another objective of this invention is to produce linear alkylaromatics that are suitable for use in the manufacture of LABS for detergents. A third objective of this invention is to maximize the production of linear alkylaromatics while minimizing the by production of non-linear alkylaromatics. More specifically, this third objective of this invention is to prepare linear alkylbenzenes by the alkylation of benzene with an olefin where alkylation proceeds with at least 98% conversion of olefin, at least 85% selectivity of olefin conversion to monoalkylbenzenes, and with at least 90% linearity with respect to monoalkylbenzene formation. A fourth objective of this invention is to produce a linear alkylaromatic fraction having a minimal, preferably nil, bromine index. A fifth objective of this invention is to decrease the quantity of catalyst that is required for alkylation.

Accordingly, this invention is a process for producing alkylaromatics. Feed olefins and feed aromatics react to form alkylaromatics in a first alkylation zone in the presence of a first alkylation catalyst at first alkylation conditions including a first temperature. An effluent stream comprising alkylaromatics and polymeric byproducts is withdrawn from the first alkylation zone. The effluent has an effluent linearity, and an effluent concentration of polymeric byproducts. At least a portion of the effluent stream comprising alkylaromatics and polymeric byproducts contacts a second alkylation catalyst at second alkylation conditions in a second alkylation zone. The second alkylation conditions comprise a second temperature that is greater than the first temperature. A polymer-depleted stream comprising alkylaromatics and heavy alkylate is withdrawn from the second alkylation zone. The polymer-depleted stream has a polymer-depleted linearity that is not greater than the effluent linearity. The polymer-depleted stream also has a polymer-depleted concentration of polymeric byproducts that is less than the effluent concentration. The polymer-depleted stream is separated into a heavy alkylate stream enriched in heavy alkylate and into a product stream depleted in heavy alkylate that contains a substantial portion of the alkylaromatics. The product stream is recovered from the process.

INFORMATION DISCLOSURE

LAB processes are described in the book edited by R. A. Meyers entitled *Handbook of Petroleum Refining Processes*, published by The McGraw-Hill Companies (New York, 1997) and in *Ullmann's Encyclopedia of Industrial Chemistry*, Volumes A8 and A13, Fifth Edition, published by VCH, (Weinheim, Germany. Flow schemes are illustrated in U.S. Pat. No. 3,484,498 issued to R. C. Berg; U.S. Pat. No. 3,494,971 issued to E. R. Fenske; U.S. Pat. No. 4,523,048 issued to B. V. Vora which teaches use of a selective diolefin hydrogenation zone; U.S. Pat. No. 5,012,021 issued to B. V. Vora which teaches use of a selective monoolefin hydrogenation zone; and U.S. Pat. No. 5,276,231 issued to J. A. Kocal et al. which teaches use of an aromatic byproducts removal zone.

The use of two alkylation reactors for the production of detergent alkylate in the presence of HF is described at page 101 in the article entitled "Alkylation," written by H. U. Hammershaimb et al., starting at page 85 in Volume 2 of *Kirk-Othmer Encyclopedia of Chemical Technology*, Fourth Edition, edited by J. I. Kroschwitz and M. Howe-Grant, published by John Wiley and Sons, New York, in 1992. A first-stage reactor completes the major part of the alkylation reaction, and in the second-stage reactor the last traces of unsaturated hydrocarbons react, and a sizable portion of the soluble polyaromatics is removed.

A fixed bed of acid-activated clay at 338–392° F. (170–200° C.) can be used to remove olefins from and decolorize a BTX (benzene-toluene-xylene) stream, as disclosed in Table 3 on page 1906 of the article entitled "Acid-Activated Clays," by D. R. Taylor and D. B. Jenkins, starting at page 1901 of Transactions, Society of Mining Engineers of AIME, Vol. 282. The article entitled, "Attapulgite: Its Properties and Applications," by W. L. Haden, Jr. and I. A. Schwint, starting at page 58 of Industrial and Engineering Chemistry, Vol. 59, No. 9, September 1967, discloses at page 68 that attapulgite can be used for the selective removal of gum-forming diolefins and acetylenes from petroleum stocks by polymerization without removing the high octane monoolefins.

A sales bulletin entitled "High Purity Aromatics," dated April, 1993, by Sud-Chemie AG, Munchen, Germany describes the purification of benzene-toluene-xylene (BTX) and cumene products by using TONSIL COG-A bleaching earth to remove unsaturated compounds like olefins and alkenylaromatics by an acidic catalyzed reaction in the form of oligomerization and/or alkylation of aromatics.

DETAILED DESCRIPTION OF THE INVENTION

It is well known that polymeric byproducts are formed during the catalytic alkylation of aromatics with olefins. For instance, the article entitled, "UOP Discloses New Way To Make Linear Alkylbenzene," by Dr. Herman S. Bloch, starting at page 79 of the Jan. 16, 1967, issue of "The Oil and Gas Journal" states that the product of an HF alkylation process which alkylates benzene with olefins obtained by dehydrogenating $C_{10}$ to $C_{13}$ normal paraffins includes polymeric byproducts. The nature of the particular polymeric byproducts that are formed in alkylation is not essential to this invention. Without limiting this invention in any way, these polymeric byproducts are believed to include, for example, dimers, trimers and tetramers of the olefinic hydrocarbons in the olefinic feedstock and thus may be viewed in large part as oligomerized normal olefins. The polymeric byproducts are believed to include mostly monoolefins but may also include diolefins, triolefins, and higher olefins. Although some of the polymeric byproducts may be linear or cyclic hydrocarbons, it is believed that most of the polymeric hydrocarbons are acyclic and non-linear (i.e., branched) hydrocarbons. The polymeric byproducts are believed to include the products of cracking dimers, trimers, and tetramers. Consequently, the number of carbon atoms in the polymeric byproducts is not necessarily an integer multiple of the number of carbon atoms in the olefin feedstock but may range broadly from the number of carbon atoms in the olefin feedstock with the fewest carbon atoms, or less, to four times the number of carbon atoms in the olefin feedstock with the most carbon atoms, or more. Some polymeric byproducts may be more detrimental than others in raising the bromine index of the LAB product or in forming color bodies on sulfonation. The greater the number of double bonds in a polymeric byproduct, the higher is the bromine index for the polymeric byproducts and, it is believed, the more likely it is that the polymeric byproduct will form a color body on sulfonation. Typically, LAB alkylate has a bromine index of 10 to 15, irrespective of whether it is produced using aluminum chloride catalyst, hydrogen fluoride catalyst, or a solid alkylation catalyst. See, for example, page 104 of the previously mentioned article by H. U. Hammershaimb et al. See also, for example, page 272 of the article entitled "Detergent Alkylation," written by R. C. Berg et al., starting at page 266 in Volume 15 of *Encyclopedia of Chemical Processing and Design*, edited by J. J. McKetta and W. A. Cunningham, published by Marcel Dekker, Inc., New York, in 1982. The article by R. C. Berg et al. also reports a change in Saybolt color from +30 for linear detergent alkylate to +26 after sulfonation of the linear detergent alkylate to sodium alkylbenzene sulfonate.

The particular side reactions that lead to the formation of the polymeric byproducts are also not essential to this invention. Again, without limiting this invention in any way, a mention of some of the competing reactions which accompany alkylation of aromatics with alkenes in the presence of HF and sulfuric acid and which might in part provide a mechanism for the formation of polymeric byproducts is found at pages 54 to 56 in Chapter XIV entitled "Alkylation of Aromatics with Alkenes and Alkanes," by S. H. Patinkin and B. S. Friedman in *Friedel-Crafts and Related Reactions*, ed. by G. A. Olah, Vol. 11, Part 1, Interscience Publishers, New York, 1964. These competing reactions include fragmentation, hydrogen transfer (producing alkanes and diolefins), polymerization, and cyclization. Acid-catalyzed oligomerization of alkenes via a carbocationic mechanism, as well as base- and metal-catalyzed oligomerization are described at pages 524 to 534 in Chapter 12 entitled "Oligomerization and Polymerization," in *Hydrocarbon Chemistry*, by G. A. Olah and A. Molnar, John Wiley and Sons, Inc., New York, 1995. Although some commercially available alkylation catalysts are more selective than others at minimizing the formation of polymeric byproducts, it is believed that these byproducts are formed at least to a small extent at suitable alkylation conditions in the presence of most, if not all, commercially available alkylation catalysts. Since it is an economic advantage to operate the alkylation zone at conditions that produce a high conversion of the olefinic feedstock and a high yield of the desired alkylaromatics, these polymeric byproducts are produced at least to a small extent in most, if not all, commercial aromatic alkylation zones.

The feedstocks which are used in the practice of this invention normally result from the dehydrogenation of paraffins. The entire dehydrogenation 1o reaction mixture is often used with the dehydrogenation reaction not being run to completion to minimize cracking, isomerization, and other undesirable and deleterious byproducts. The branched olefins which are formed in dehydrogenation are not removed, yet the total amount of nonlinear alkylbenzene formed must still be sufficiently small that the monoalkylate meets the requirements of 90% linearity. The polyolefins formed during dehydrogenation are minimized in the feedstocks used in the practice of this invention. Consequently the feedstocks are a mixture largely of unreacted paraffins, small amounts (ca. 2%) of branched olefins, and unibranched, linear monoolefins which typically are in the $C_6$–$C_{20}$ range, although those in the $C_8$–$C_{16}$ range are preferred in the practice of this invention, and those in the $C_{10}$–$C_{14}$ range are even more preferred. Unsaturation may appear anywhere on the linear monoolefin chain; there is no requirement as to the position of the double bond, but only a requirement as to the linearity of the olefin. See pages 1.53–1.66 and 5.11–5.19 in the previously mentioned book edited by R. A. Meyers entitled *Handbook of Petroleum Refining Processes*.

The linear monoolefins in the feedstock are reacted with benzene.

Although the stoichiometry of the alkylation reaction requires only 1 molar proportion of benzene per mole of total linear monoolefins, the use of a 1:1 mole proportion results in excessive olefin polymerization and polyalkylation. That is, the reaction product under such conditions would consist not only of the desired monoalkylbenzenes, but also large amounts of the dialkylbenzenes, trialkylbenzenes, possibly higher polyalkylated benzenes, olefin dimers, trimers, etc., and unreacted benzene. On the other hand, it is desired to have the benzene:olefin molar ratio as close to 1:1 as possible to maximize benzene utilization and to minimize the recycle of unreacted benzene. The actual molar proportion of benzene to total monoolefins will therefore have an important effect on both conversion and, perhaps more importantly, selectivity of the alkylation reaction. In order to carry out alkylation with the conversion, selectivity, and linearity required using the catalysts of our process, a total benzene:linear monoolefin molar ratio of from 5:1 up to as high as 30:1 is recommended, although the process normally operates satisfactorily at a total benzene-:linear monoolefins molar ratio between about 8:1 and about 20:1.

The benzene and linear monoolefins are reacted in a first reaction zone in the presence of a catalyst under alkylation conditions to produce an alkylation reactor effluent stream that comprises alkylaromatics, which are the desired product, and polymeric byproducts. The effluent of the first alkylation reactor has a bromine index, on a paraffin-free and benzene-free basis, in the range of generally from 240/MW to 1200000/MW, where MW is the average molecular weight of the alkylaromatics in the effluent stream. The molecular weight of the alkylaromatics can be computed by persons of ordinary skill in the art from the distribution of the individual alkylaromatics in the effluent stream as determined by gas chromatography and by the molecular weights of the individual alkylaromatics. More typically, the bromine index on a paraffin-free and benzene-free basis of the first alkylation reactor effluent is from 7200/MW to 240000/MW, where MW is the average molecular weight of the alkylaromatics in the effluent stream.

The particular catalyst and the particular alkylation conditions are not critical to the success of this invention, and any suitable catalyst and conditions can be used, provided that the alkylation reactor effluent stream comprises alkylaromatics and polymeric byproducts. The reaction conditions, including the water content and in particular the reaction temperature, depend in part on the particular catalyst, and thus the suitable reaction temperature can vary widely. For a liquid alkylation catalyst such as HF suitable temperatures range generally between about 60 and about 150° F. (16 and 66° C.) and usually between about 100 and about 150° F. (38 and 66° C.). For a solid alkylation catalyst suitable temperatures include a temperature in the range of generally between about 176 and 320° F. (80 and 160° C.) and usually between about 212 and 302° F. (100 and 150° C.). Although alkylation can be conducted in the vapor phase or as a mixed vapor-liquid phase, in general alkylation is conducted as a liquid phase process and pressures must be sufficient to maintain the reactants in the liquid state. The requisite pressure necessarily depends upon the feedstock and temperature, but generally is in the range of 0–1000 psi(g) (0–6895 kPa(g)), and usually 100–400 psi(g) (689–2758 kPa(g)).

Because the detergent alkylation reaction is exothermic, a temperature rise may occur in the alkylation reactor. The magnitude of the temperature rise above the temperature of the reactants charged to an adiabatic alkylation reactor depends on several factors including especially the benzene:olefin molar ratio. In general, the higher the benzene:olefin molar ratio the smaller is the adiabatic temperature rise, because the greater the excess of benzene the greater is the heat sink relative to the exothermic heat of reaction. Likewise, the higher the paraffin:olefin molar ratio, the smaller is the adiabatic temperature rise. Most continuous commercial alkylation reactors are adiabatic, by which in the context of a continuous flow reactor is meant that no heat is added or subtracted from the reactor, except for insignificant heat losses to the ambient environment and except for the heat carried by streams that enter and exit the reactor. Such streams include the reactor feed and effluent streams, and in the case of liquid acid catalysts, the circulating acid streams. In commercial detergent alkylation reactors, the temperature rise is typically less than 27° F. (15° C.) and often less than 14.4° F. (8° C.). Generally, the temperature of the reactor effluent stream equals the temperature of the reactant charge stream plus the temperature rise, if any, in the alkylation reactor.

Although the alkylation can take place in the presence of a liquid alkylation catalyst, such as HF or sulfuric acid, the alkylation preferably takes place in the presence of a solid alkylation catalyst. Solid alkylation catalysts typically are characterized as having an acid function and are, therefore, better known as solid acid catalysts. Such solid acid catalysts include, but are not limited to, materials such as amorphous silica-alumina, crystalline aluminosilicate materials such as zeolites and molecular sieves, naturally occurring and man-made clays including pillared clays, sulfated oxides such as sulfonated zirconia, traditional Friedel-Crafts catalyst such as aluminum chloride and zinc chloride, and solid Lewis acids generally. The nature of the solid alkylation catalyst is not critical to the success of this invention and is largely a matter of choice to be made by the practitioner. Solid alkylation catalysts are illustrated in U.S. Pat. No. 3,201,487 issued to S. Kovach et al.; U.S. Pat. No. 4,358,628 issued to L. Slaugh; U.S. Pat. No. 4,489,213 issued to S. Kovach; U.S. Pat. No. 4,673,679 issued to D. Farcasiu; U.S. Pat. No. 5,003,121 issued to Imai et al. which discloses an extruded catalyst comprising clay and at least one multi-valent metal; U.S. Pat. No. 5,034,564 issued to J. A. Kocal which discloses a catalyst comprising a pillared clay and a binder; U.S. Pat. Nos. 5,196,574 and 5,344,997, both issued to J. A. Kocal, which disclose a fluorided silica-alumina catalyst and whose teachings are incorporated herein by reference; U.S. Pat. No. 5,302,732 issued to K. Z. Steigleder et al. which describes an ultra-low sodium silica-alumina catalyst and whose teachings are incorporated herein by reference; and U.S. Pat. No. 5,491,271 issued to Marinangeli et al. which discloses the use of either delaminated or pillared tetrahedrally charged clays. Zeolitic solid alkylation catalysts are disclosed in U.S. Pat. Nos. 3,751,506; 4,387,259; and 4,409,412; and in addition in U.S. Pat. No. 5,019,670 and U.S. Pat. No. 5,132,477, which disclose using MCM-22 to alkylate aromatics with olefin oligomers; and also in U.S. Pat. Nos. 4,301,317 and 4,301,316, which describe catalyzing detergent alkylation with crystalline aluminosilicates. Silica-aluminas used as a support for various metals in the alkylation of aromatics with olefins include U.S. Pat. Nos. 3,169,999; 3,201,487; 4,358,628; and 4,870,222; European Patent Application No. 0160145; Japanese Patent Application J02237641-A; and articles by Kurosaki and Okazaki in *Bull Chem. Soc. Japan*, 63, 2363 (1990) and *Chemistry Letters*, 589 (1991).

A fluorided silica-alumina catalyst, particularly one with a weight ratio of silica to alumina in the range of at least 1:1 (50 weight percent) up to as high as 9:1 (90 weight percent) containing from 1 to 6 weight percent fluoride, is particularly effective in the liquid phase alkylation of benzene by linear olefins to produce linear alkyl benzenes at temperatures no greater than 284° F. (140° C.). See U.S. Pat. Nos. 5,196,574 and 5,344,997, the teachings of which are incorporated herein by reference. The stated silica-alumina weight ratio range is a useful compromise between selectivity and activity. Selectivity of the fluorided silica-aluminas of this preferred catalyst increases with increasing silica content, which recommends or suggests the use of as high a silica level as possible. However, the activity of the fluorided materials increases initially, appears to pass through a maximum at about a 3:1 ratio of silica:alumina, and then decreases thereafter. Accordingly, although fluorided silica-aluminas can be used throughout the given range, those having a silica to alumina weight ratio between about 65:35 and 85:15 are preferred for this catalyst.

Preferably, this preferred fluorided silica-alumina catalyst contains from about 1 up to 6 weight percent fluoride based on volatile-free finished silica-alumina catalyst. Higher fluoride levels may be used but without any substantial incremental benefit. The preferred fluoride level depends on the silica-alumina ratio. For example, for a 75:25 silica:alumina ratio fluoride levels between about 1.5 and 3.5 are preferred.

An amorphous, cogelled, oil-dropped silica-alumina is preferred for the fluorided silica-alumina catalysts. Other silica-aluminas of the same apparent composition may be used, but generally are inferior to the amorphous, cogelled, oil-dropped product. The oil-drop method of preparing, for example, aluminas is an old, tried and true method dating to U.S. Pat. No. 2,620,314, and therefore will not here be discussed in great detail. The following description will be familiar to one practicing this art and will serve as a general description of the subject method.

The cogelled silica-alumina composition is suitably prepared as spheroidal particles by the well-known oil-drop method. In a preferred method of manufacture, an alumina sol, utilized as an alumina source, is commingled with an acidified water glass solution as a silica source, and the mixture is further commingled with a suitable gelling agent, for example, urea, hexamethylenetetramine (HMT), or mixtures thereof. The mixture is discharged while still below gelatin temperature by means of a nozzle or rotating disk, into a hot oil bath maintained at or above gelatin temperature. The mixture is dispersed into the hot oil bath as droplets which form into spherical gel particles. The alumina sol is preferably prepared by a method wherein aluminum pellets are commingled with a quantity of treated or deionized water, with hydrochloric acid being added thereto in a sufficient amount to digest a portion of the aluminum metal and form the desired sol. A suitable reaction rate is effected at about reflux temperature of the mixture.

The spheroidal gel particles prepared by the oil-drop method are aged, usually in the oil bath, for a period of at least 10–16 hours, and then in a suitable alkaline or basic medium for at least 3 to about 10 hours, and finally water washed. Proper gelatin of the mixture in the oil bath, as well as subsequent aging of the gel spheres, is not readily accomplished below about 122° F. (50° C.), and at about 212° F. (100° C.), the rapid evolution of the gases tend to rupture and otherwise weaken the spheres. By maintaining sufficient superatmospheric pressure during the forming and aging steps in order to maintain water in the liquid phase, a higher aging temperature may be employed, frequently with improved results. If the gel particles are aged at superatmospheric pressure, no alkaline aging step is required.

The spheres are water-washed, preferably with water containing a small amount of ammonium hydroxide and/or ammonium nitrate. After washing, the spheres are dried, at a temperature from about 185 to about 482° F. (85 to 250° C.) for a period from about 6 to about 24 hours or more, and then calcined at a temperature from about 572 to about 1400° F. (300 to 760° C.) for a period from about 2 to about 12 hours or more.

The fluorided silica-alumina catalysts are prepared by impregnating the silica-alumina with essentially hydrogen fluoride. This is not to say that HF is the only fluoride source, but rather that the fluoride source is equivalent to HF in affording a fluorided silica-alumina free of additional metals or metallic species and which analytically contains only additional HF. Examples of a suitable fluoride source, in addition to HF, include ammonium fluoride [$NH_4F$], ammonium bifluoride [$NH_4HF_2$], and organic fluorides. When an ammonium fluoride is used $NH_3$ is volatilized during subsequent heating of the fluoride-impregnated silica-alumina. When organic fluorides are used the impregnated silica-alumina is subsequently heated under conditions which oxidize carbon to carbon dioxide and excess hydrogen to water, both of which volatilize to leave the equivalent of an HF-impregnated product.

The preparation of the fluorided silica-alumina catalyst may be performed by a variety of procedures, depending upon the fluoride source, fluoride level sought, and so forth. For example, when an ammonium fluoride is used equal volumes of the silica-alumina and an aqueous solution of the ammonium fluoride containing the desired amount of fluoride are intimately mixed, (e.g., cold rolled) and the mixture subsequently heated to evaporate the water. The resulting fluoride-impregnated product may be dried at 257 to 347° F. (125 to 175° C.) for several hours, and then calcined at a temperature typically in the 662 to 1022° F. (350 to 550° C.) range for 1–6 hours, depending on the temperature used. For calcination near 752° F. (400° C.) the time generally is about 3 hours. It is found that ammonia is lost from the catalyst when the impregnated material is heated to about 302° F. (150° C.). No significant amounts of fluoride are lost up to a temperature of about 1022° F. (550° C.) but fluoride loss is observed at higher temperatures.

When HF is the fluoride source a similar impregnation method may be used, although it is also possible to fluoride the catalyst with a gaseous HF stream. In the latter instance no drying step is necessary and the fluorided material may be calcined directly. Where an organic fluoride is used, the silica-alumina may be impregnated using either a vapor phase or liquid phase source of fluoride. For example, an organic fluoride such as t-butyl fluoride can be impregnated from its solution in a volatile solvent, the solvent subsequently removed by evaporation, the silica-alumina heated to remove the last traces of solvent and then calcined to remove the organic material. This procedure is similar to impregnation using inorganic fluoride but may suffer from fluoride loss on calcination. Alternatively, the t-butyl fluoride may be volatilized, and HF deposited on the silica-alumina via thermal decomposition of the t-butyl fluoride. Fluoride levels can be controlled by gas rate, time and temperature of exposure.

It has been found that these fluorided silica-alumina catalysts are quite sensitive to water. Thus it is desirable that the feedstocks be dried to a level of 1 ppm or less. With increasing feedstock water content the catalysts are found to deactivate. It is also quite desirable to dry the catalyst thoroughly immediately prior to use. This can be successfully done by heating the catalysts in a dry, unreactive gas such as air or nitrogen at a temperature of at least 302° F. (150° C.), but preferably at even higher temperatures. The time needed for adequate drying will depend on such factors as gas flow rate and temperature, but at 572° F. (300° C.) a time from 6 to about 12 hours appears adequate.

Another preferred class of catalysts includes silica-aluminas having an ultra-low sodium content less than about 0.1 weight percent. See U.S. Pat. No. 5,302,732, the teachings of which are incorporated herein loy reference. The silica-aluminas may contain a weight ratio of silica to alumina of at least 1:1 up to as high as 19:1, but a silica:alumina ratio of 2:1 (67:33) up to about 19:1 (ca. 95:5) is preferred. For these ultra-low sodium catalysts, an amorphous, cogelled, silica-alumina is preferred. The cogelled silica-alumina composition is suitably prepared as spheroidal particles by the oil-drop method followed by aging, washing drying, and calcining, in a manner similar to that hereinbefore described. Fluorided silica-aluminas, such as silica-aluminas prepared by impregnating the silica-alumina with essentially hydrogen fluoride as described hereinbefore, may also be used for these ultra-low sodium catalysts. Where fluorided silica-aluminas are utilized as catalysts the fluoride, expressed as fluorine, is present at levels from about 1 up to as high as about 6 weight percent, and in the most usual case fluorine is present at levels from about 1.5 up to about 3.5 weight percent. But the sodium content must be less than about 0.1 weight percent, although it is preferred to use silica-aluminas, whether or not fluorided, with a sodium content no more than about 0.05 weight percent, and it is still more highly preferred to use silica-aluminas with a sodium content no more than about 0.03 weight percent. The ultra-low sodium silica-aluminas may be readily prepared by several methods. One method is to wash the oil-aged spheres well with aqueous ammonium hydroxide-ammonium nitrate so that a low sodium concentration is reached in the calcined base. Standard chemical and engineering techniques (such as having sufficient ammonium hydroxide and ammonium nitrate, high linear velocity of the wash solution, and an adequate volume of wash water for the volume of spheres treated) are used to ensure efficient washing. Another method is to wash the calcined base to remove sodium. This approach is similar to removing sodium from a zeolite or to any other cation exchange process where $H^+$ or $NH_4^+$ is exchanged for an alkali or alkaline earth metal cation. The aqueous wash solution may contain HCl, $NH_4NO_3$, $NH_4Cl$, $HNO_3$, $(NH_4)N_3$, for example, and exchange may be accomplished by cycling the wash solution through a packed bed of the calcined base followed by a water rinse using techniques well known to the skilled worker. Although the first described method is, at least in theory, the preferred choice, the actual method used will depend, for example, on available equipment, the particular physical properties sought in the final preparation, extraneous manufacturing considerations, and so on. The ultra-low sodium silica-alumina catalysts are preferably employed in a packed bed as spheres, in particular as spherical particles no more than about 1/16 in (1.59 mm) in diameter, and more desirably as spherical particles with a diameter of less than 1/16 in (1.59 mm) including spherical particles with a diameter no more than about 1/32 in (0.79 mm).

Solid catalysts used for alkylation of aromatic compounds by olefins, especially those in the 6 to 20 carbon atom range, usually are deactivated by by-products which are preferentially adsorbed by the catalysts. Such by-products include, for example, polynuclear hydrocarbons in the 10 to 20 carbon atom range formed in the dehydrogenation of $C_6$ to $C_{20}$ linear paraffins and also include products of higher molecular weight than the desired monoalkyl benzenes, e.g., di- and tri-alkyl benzenes, as well as olefin oligomers. Although it can be readily appreciated that such catalyst deactivating agents or "poisons" are an adjunct of aromatic alkylation, fortunately it has been observed that deactivating agents can be readily desorbed from many solid alkylation catalysts by washing the catalyst with the aromatic reactant. In particular, the preferred silica-alumina and fluorided silica-alumina catalysts for use in this invention can be reactivated in this manner. Thus, catalyst reactivation, or catalyst regeneration as the term is more commonly employed, is conveniently effected by flushing the catalyst with aromatic reactants to remove accumulated poisons from the catalyst surface, generally with restoration of 100% of catalyst activity.

The effluent stream that is withdrawn from the first alkylation reaction zone contains alkylaromatics and polymeric byproducts. The linearity of the effluent stream is generally greater than 85% and more usually greater than 90%. The molar ratio of polymeric byproducts per alkylaromatic in the effluent stream of the first alkylation reaction zone is generally less than 0.05:1. The effluent of the first alkylation reaction zone may contain little, or no measurable feed olefin because the feed olefin conversion in the first alkylation reactor is generally high. Nevertheless, the first alkylation reactor effluent stream may contain feed olefins. However, the molar ratio of feed olefin per alkylaromatic in the first reactor effluent stream generally is less than 0.1:1.

Generally, at least a portion, and preferably an aliquot portion, of the first alkylation reactor effluent stream passes to the second alkylation reaction zone. An aliquot portion of the first alkylation reactor effluent stream is a portion of the first alkylation reactor effluent stream that has essentially the same composition as the first alkylation reactor effluent stream. More preferably, the entire first alkylation reactor effluent stream passes to the second alkylation reaction zone. In addition to any feed aromatics and/or any feed olefins in the portion of the first alkylation reactor effluent stream that passes to the second alkylation reaction zone, additional feed aromatics and/or additional feed olefins may optionally be introduced into the second alkylation reaction zone. Such additional feed aromatics and/or feed olefins may be introduced via one or more separate makeup streams. Of course, preferably no such additional feed olefins are introduced into the second alkylation reaction zone, but if feed olefins are introduced into the second alkylation reaction zone, then the molar ratio of feed olefin per alkylaromatic introduced into the second alkylation reaction zone may be less than 0.1:1. Alternatively, if feed olefins are introduced into the second alkylation reaction zone, the amount of feed olefins introduced may be less than the amount which, if combined with the portion of the first alkylation reactor effluent stream that is passed to the second alkylation reaction zone to form a combined stream, would form a combined stream which would have a bromine index within the ranges previously stated herein for the bromine index of the effluent of the first alkylation reactor.

Without being limited to any particular theory or mechanism, it is believed that the alkylaromatics and polymeric byproducts may react in the second reaction zone in the presence of a catalyst under conditions to produce heavy alkylate, and thus the second alkylation reactor effluent comprises heavy alkylate and alkylaromatics, which are the desired product. If feed aromatics are also introduced into the second alkylation reaction zone, the feed aromatics may also react with the polymeric byproducts to form heavy alkylate. The concentration of polymeric byproducts in the second alkylation reaction zone effluent stream is less than that in the first alkylation reaction zone effluent stream, and accordingly the second alkylation reaction zone is often referred to herein as the polymer-depleted stream. The polymer-depleted stream has a bromine index, on a paraffin-free and feed-aromatic-free (e.g., benzene-free) basis, in the range of generally from 0 to 240000/MW, where MW is the average molecular weight of the alkylaromatics in the polymer-depleted stream. More typically, the bromine index on a paraffin-free and feed-aromatic-free basis of the polymer-depleted stream is from 0 to 48000/MW, where MW is the average molecular weight of the alkylaromatics in the polymer-depleted stream.

In the second alkylation reaction zone, the particular catalyst and the particular alkylation conditions are not critical to the success of this invention, and any suitable catalyst and conditions can be used that produce a second alkylation reactor effluent stream comprising alkylaromatics and heavy alkylate. The catalyst in the second alkylation reaction zone may be any of the suitable catalysts previously described for the first alkylation reaction zone, including the preferred catalysts comprising silica-alumina or fluorided silica-alumina. The reaction conditions, which depend in part on the particular catalyst, produce a polymer-depleted stream having a lower concentration of polymeric byproducts than the first alkylation reaction zone effluent stream. In addition, the linearity of the polymer-depleted stream is the same as or less than (i.e., not greater than) the first alkylation reaction zone effluent stream. Generally, the linearity of the polymer-depleted stream is generally less than 2%, preferably less than 1%, more preferably less than 0.5%, and even more preferably less than 0.1% less than the linearity of the first alkylation reaction zone effluent stream.

The second alkylation reaction temperature is higher than that for the first alkylation reaction zone. The second alkylation reaction zone temperature is generally at least 9° F. (5° C.), may in some cases be at least 36° F. (20° C.), and may be up to 90° F. (50° C.) higher than the first alkylation reaction zone temperature. Preferably, the lowest temperature of the temperature(s) of the location(s) where aromatics react with polymeric byproducts to produce heavy alkylate in the catalyst bed of the second alkylation reaction zone is greater than the highest temperature of the temperature(s) of the location(s) where feed aromatics react with feed olefins to form alkylaromatics in the catalyst bed of the first alkylation reaction zone. For example, suppose the temperatures of the locations where benzene reacts with feed olefins to form alkylaromatics in the first alkylation reaction zone catalyst bed range from 212° F. (100° C.) to 221° F. (105° C.). Then, preferably the temperatures of the locations where aromatics react with polymeric byproducts to produce heavy alkylate in the second alkylation reaction zone catalyst bed are generally greater at least 230° F. (110° C.), may in some cases be at least 257° F. (125° C.), and may be up to 311° F. (155° C.). The higher second alkylation reaction temperature may be achieved by any suitable heating, e.g., heating of one or more streams entering the second alkylation reaction zone or heating of the catalyst bed in the second alkylation reaction zone. For a liquid alkylation catalyst such as HF suitable temperatures range generally between about 100 and about 180° F. (38 and 82° C.) and usually between about 120 and about 160° F. (49 and 71° C.). For a solid alkylation catalyst suitable temperatures include a temperature in the range of generally between about 212 and 356° F. (100 and 180° C.) and usually between about 248 and 338° F. (120 and 170° C.). Although alkylation can be conducted in the vapor phase or as a mixed vapor-liquid phase, in general alkylation is conducted as a liquid phase process and pressures must be sufficient to maintain the reactants in the liquid state. The requisite pressure necessarily depends upon the feedstock and temperature, but generally is in the range of 0–1000 psi(g) (0–6895 kPa(g)), and usually 100–400 psi(g) (689–2758 kPa(g)).

There is no requirement that the catalyst in the first and second reaction zone be the same catalyst. However, the catalyst in the second alkylation reaction zone may be the same composition as the catalyst in the first alkylation reaction zone. In this case, the temperature of the second alkylation reaction zone is generally up to about 90° F. (50° C.), and normally from about 9° F. to about 90° F. (5 to 50° C.), greater than the temperature of the first alkylation reaction zone.

Alkylation of benzene by the linear monoolefins in either the first or the second alkylation reaction zone with the preferred catalysts may be conducted either as a batch method or in a continuous manner. The catalysts may be used as a packed bed or a fluidized bed. Feedstock to the reaction zones may be passed either upflow or downflow, or even horizontally as in a radial bed reactor. In one desirable variant, the feed olefin may be fed into several discrete points within the reaction zone, and at each zone the benzene:olefin ratio may be greater than 30:1. However, the total benzene:olefin ratio used in the foregoing variant will still be within the stated range. With a solid alkylation catalyst in the first alkylation reaction zone and the catalyst in a packed bed, the total feed mixture, that is, benzene plus feedstock containing linear monoolefins, is passed through the first alkylation zone's packed bed at a LHSV of generally between about 0.5 and about 20 $hr^{-1}$. As used herein, the abbreviation 'LHSV' means liquid hourly space velocity, which is defined as the volumetric flow rate of liquid per hour divided by the catalyst volume, where the liquid volume and the catalyst volume are in the same volumetric units. The optimum LHSV depends upon alkylation temperature, how long the catalyst has been used, the ratio of silica to alumina and fluoride level in the catalyst, and so on, and normally the LHSV ranges between about 2 and about 10 $hr^{-1}$ in the first alkylation reaction zone. For the case of a solid alkylation catalyst in a packed bed in the second alkylation reaction zone, the total feed mixture, that is, the portion (which is usually an aliquot portion) of the first alkylation effluent and any additional feed aromatic that is passed to the second alkylation zone, the LHSV is generally between about 5 and about 50 $hr^{-1}$ and normally between about 10 and about 30 $hr^{-1}$. An aliquot portion of the first alkylation effluent is a portion of the first alkylation effluent that has essentially the same composition as the first alkylation effluent.

The polymer-depleted stream that is withdrawn from the second alkylation reaction zone generally contains alkylaromatics and heavy alkylate. The polymer-depleted stream may also contain feed aromatics and paraffins. The polymer-depleted stream is passed to conventional product recovery facilities for the recycling of the feed aromatic and the recovery of the alkylaromatics from the heavy alkylate and the paraffins. These conventional product recovery facilities are known to persons of ordinary skill in the art of detergent alkylation. Since the alkylation reaction goes to at least 98% conversion, little unreacted monoolefin is recycled with paraffin.

EXAMPLES

The following examples are illustrative only. They show in some detail how the invention may be carried out but are not intended to limit the invention as set forth in the claims.

Example 1

Example 1 of U.S. Pat. No. 5,302,732, at Col. 11, Line 27 to Col. 12, Line 4, describing a preparation of ultra-low sodium silica-alumina is incorporated herein by reference. The following procedure is typical of that used to prepare silica-aluminas with a low sodium content and utilizes an ammonium nitrate wash of the calcined base. A 75:25 silica-alumina was washed with a 15 weight percent aqueous ammonium nitrate solution in an amount such that the total weight of ammonium nitrate was equal to the weight of the silica-alumina being washed. The wash solution (as well as the rinse) temperature was 190° F. (88° C.) and was pumped upflow through a bed of silica-alumina at a linear velocity of 1 cm/min. for 5 hours with recycle of the used wash solution. The silica-alumina was contained in a column of 1 in (25.4 mm) diameter and had a volume of approximately 165 cc. After the wash was complete, the silica-alumina was rinsed with 3–4 volumes of deionized water at 190° F. (88° C.) pumped upflow at a linear velocity of 1 cm/min. The washed catalyst was oven dried at 300° F. (149° C.) for 4 hours. For one sample the wash solution was 1 normal hydrochloric acid instead of 15% ammonium nitrate. Table 1 summarizes the sodium content of the silica-alumina before treatment and after being washed and rinsed as described.

TABLE 1

SODIUM CONTENT OF SILICA-ALUMINA
$NH_4NO_3$ WASH EXPERIMENTS

| SAMPLE | SAMPLE TREATMENT | Na, wt % |
|---|---|---|
| A | NONE | 0.20 |
| B | Standard Wash | 0.03 |
| C | Standard Wash | 0.03 |
| D | Standard Wash | 0.04 |
| E | Standard Wash except 20 wt-% $NH_4NO_3$ and 10 cm/min wash and rinse velocity | 0.03 |
| F | Standard wash except 1.0 N HCl | 0.01 |

These results show that it is possible to routinely obtain a sodium content of 0.03 weight percent on a silica-alumina using the described procedure. Where the wash solution is one normal hydrochloric acid instead of the standard ammonium nitrate an even lower sodium value of 0.01 weight percent can be obtained, but at these conditions there is also some dissolution of alumina.

Example 2

Example 3 of U.S. Pat. No. 5,302,732 at Col. 12, Line 64 to Col. 13, Line 27, describing the preparation of two catalysts of different sizes and sodium contents, is incorporated herein by reference. A sample of 75:25 silica-alumina was oil dropped so as to afford 1/32 in (0.79 mm) diameter spheres. All the spheres fell through a #20 screen (0.0331 in, 0.841 mm) and on to a #25 screen (0.0278 in, 0.707 mm). The silica-alumina was treated as described in Example 1 to afford a sample of low sodium silica-alumina which was tested for its performance as described in Example 2. Table 2 summarizes the physical properties of this silica-alumina catalyst compared with another, similar silica-alumina catalyst but having a 1/16 in (1.59 mm) diameter.

TABLE 2

| Catalyst | M | N |
|---|---|---|
| ABD, g/cc | 0.53 | 0.50 |
| Na, wt-% | 0.04 | 0.02 |
| Diameter, in. | 1/16 | 1/32 |
| BET Surface Area, $m^2/g$ | 339 | 371 |

In the following examples, linearity is reported on a weight basis. Thus, in Examples 3–7, linearity equals the weight of linear monoalkyl benzene produced divided by the weight of monoalkyl benzene produced multiplied by 100.

Example 3—Comparative

Example 3 is a comparative example which describes the performance results of a single fixed bed reactor. A catalyst was prepared substantially according to the method of Example 2. The catalyst comprised amorphous silica-alumina (76 wt-% $SiO_2$ and 24 wt-% $Al_2O_3$), contained 96 wppm sodium, and was spherical with a nominal diameter 1/32 in (0.79 mm). The catalyst's performance was evaluated in a standard detergent alkylation pilot plant. The pilot plant test was conducted in a fixed bed reactor operating at 275° F. (135° C.), a benzene to olefin feed molar ratio of 10, a liquid hourly space velocity (LHSV) of 2.0 $hr^{-1}$, and a pressure of 500 psi(g) (3447 kPa(g)). The olefinic feed was 1-decene, which contained 96.5 wt-% linear olefins and 3.5 wt-% nonlinear olefins, as measured by gas chromatograph (GC). The results are presented in Table 3.

TABLE 3

| | |
|---|---|
| Olefin Conversion, wt-% | 99.99 |
| Linearity, wt-% | 93.3 |
| Selectivities, wt-%: | |
| LAB | 86.78 |
| Nonlinearalkyl benzene | 6.25 |
| Olefin dimer | 1.76 |
| $C_{26}$-plus heavies[1] | 5.21 |

NOTE:
[1]$C_{26}$-plus heavies includes monoalkyl benzenes, dialkyl benzenes, and olefin trimer.

The bromine index on a benzene-free and paraffin-free basis of the total alkylation reactor effluent is estimated to be 1100.

Example 4—Comparative

Example 4 is a comparative example which describes the performance results of a second fixed bed reactor operating at temperatures that are the same as or less than that of the single fixed bed reactor in Example 3. A catalyst was 5 prepared substantially according to the method described herein for a fluorided silica-alumina catalyst. The catalyst comprised amorphous silica-alumina (73.3 wt-% $SiO_2$ and 23.6 wt-% $Al_2O_3$), contained 3.1 wt-% fluoride, and was spherical with a nominal diameter 1/16 in (1.59 mm). The performance of a sample of the catalyst was evaluated in a standard detergent alkylation pilot plant with a fixed bed reactor. The feed was the total alkylation reactor effluent produced in Example 3. The operating conditions and results are shown in Table 4.

TABLE 4

| Operating Conditions: | A | B | C |
|---|---|---|---|
| Pressure, psi(g) (kPa(g)) | 500 (3447) | 500 (3447) | 500 (3447) |
| LHSV, $hr^{-1}$ | 4.0 | 4.0 | 2.0 |
| Temperature, ° F. (° C.) | 248 (120) | 275 (135) | 275 (135) |
| Olefin Conversion, wt-% | 100.00 | 100.00 | 100.00 |
| Linearity, wt-% | 93.1 | 93.1 | 93.1 |
| Bromine Index[1] | 470 | 400 | 340 |
| Selectivities, wt-%: | | | |
| LAB | 86.68 | 86.89 | 86.94 |
| Nonlinear alkyl benzene | 6.38 | 6.48 | 6.40 |
| Olefin dimer | 0.82 | 0.71 | 0.60 |
| $C_{26}$-plus heavies[2] | 6.12 | 5.92 | 6.06 |

NOTES:
[1]Estimated bromine index on a benzene-free and paraffin-free basis of the total alkylation reactor effluent.
[2]$C_{26}$-plus heavies includes monoalkyl benzenes, dialkyl benzenes, and olefin trimer.

Example 4 shows the results of passing the total alkylation reactor effluent of Example 3 to various relatively large second alkylation reactors that operate at temperatures that are not greater than that of the reactor in Example 3. The reactor temperature of operating conditions of A in Example 4 is lower than that of Example 3, while the reactor temperatures of operating conditions of B and C are the same as in Example 3. There is no significant difference between the linearity of the reactor effluent of Example 3 and those of Example 4. While the olefin dimer selectivities and the bromine indices of the second reactor effluents are less than those of the reactor effluent of Example 3, the bromine indices of the second reactor effluents remain relatively high at 340 to 470, despite the relatively large catalyst volumes (relatively low space velocities) that are used in the second reactors. A comparison of the operating conditions of B and C shows very little improvement in both olefin dimer selectivity and bromine index even when the volume of catalyst in the second reactor is doubled.

Example 5 — Comparative

Example 5 is a comparative example which describe the performance results of a single fixed bed reactor. The performance of a sample of the catalyst prepared in Example 4 was evaluated in a standard detergent alkylation pilot plant. The pilot plant test was conducted in a fixed bed reactor operating at 239° F. (115° C.), a benzene to olefin feed molar ratio of 30, a liquid hourly space velocity (LHSV) of 5.0 hr$^{-1}$, and a pressure of 500 psi(g) (3447 kPa(g)). The olefinic feed was obtained from a commercial alkylation unit and was produced by dehydrogenating $C_{10}$–$C_{13}$ normal paraffins, then selectively hydrogenating diolefins in the dehydrogenated product to monoolefins, and finally selectively adsorbing aromatic byproducts from the selective hydrogenation product. The composition of the olefin feed as measured by GC and by high pressure liquid chromatography (HPLC) is shown in Table 5. The bromine index of the olefin feed was 8500. The results of the pilot plant evaluation are presented shown in Table 6.

TABLE 5

| Component | Composition, wt-% |
| --- | --- |
| Paraffins | 91.3 |
| Olefins: | 8.4 |
| Distribution, % of total olefins: | |
| Linear olefins | 98.4 |
| Nonlinear olefins | 1.6 |
| Aromatics | 0.3 |

TABLE 6

| | |
| --- | --- |
| Olefin Conversion, wt-% | ≅100 |
| Linearity, wt-% | 93.6 |
| Selectivities, wt-%: | |
| LAB | 90.0 |
| Nonlinear alkyl benzene | 6.2 |
| $C_{20}$-plus heavies[1] | 3.8 |

NOTE:
[1]$C_{20}$-plus heavies includes monoalkyl benzenes, dialkyl benzenes, olefin dimer, and olefin trimer.

Example 6

A sample of the catalyst prepared in Example 4 was loaded into a standard detergent alkylation pilot plant having a fixed bed reactor, which is referred to in this Example 6 as "reactor 1". The olefinic feed to reactor 1 was the same as that in Example 5, and the operating conditions of reactor 1 are shown in Table 7. The performance of another sample of the catalyst prepared in Example 4 was evaluated in a standard detergent alkylation pilot plant with a fixed bed reactor, which is referred to in this Example 6 as "reactor 2." The feed to reactor 2 was the total alkylation reactor effluent of reactor 1, and the operating conditions of reactor 2 are shown in Table 7.

The results of D are comparative, since in D reactors 1 and 2 have the same temperature whereas in E, F, and G the temperature of reactor 2 is greater than that of reactor 1.

In all of the operating conditions of Example 6, the catalyst volume of reactor 2 is small, namely only about one-third that of reactor 1.

TABLE 7

| Operating Conditions: | D | E | F | G |
| --- | --- | --- | --- | --- |
| Reactor 1: | | | | |
| Pressure, psi(g) (kPa(g)) | 500 (3447) | 500 (3447) | 500 (3447) | 500 (3447) |
| LHSV, hr$^{-1}$ | 5.0 | 5.0 | 5.0 | 5.0 |
| Temperature, ° F. (° C.) | 257 (125) | 239 (115) | 239 (115) | 257 (125) |
| Reactor 2: | | | | |
| Pressure, psi(g) (kPa(g)) | 500 (3447) | 500 (3447) | 500 (3447) | 500(3447) |
| LHSV, hr$^{-1}$ | 15.0 | 15.0 | 15.0 | 15.0 |
| Temperature, ° F. (° C.) | 257 (125) | 284 (140) | 320 (160) | 347 (175) |
| Reactor 2 Effluent: | | | | |
| Olefin Conversion, wt-% | ≅100 | ≅100 | ≅100 | ≅100 |
| Linearity, wt-% | 92.5 | 93.7 | 92.7 | 91.3 |
| Selectivities, wt-%: | | | | |
| LAB | 89.7 | 91.4 | 90.0 | 88.9 |
| Nonlinear alkyl benzene | 7.3 | 6.1 | 7.1 | 8.5 |
| $C_{20}$-plus heavies[1] | 3.0 | 2.5 | 2.9 | 2.6 |
| Bromine index[2] | 140 | 140 | 100 | 50 |

NOTES:
[1]$C_{20}$-plus heavies includes monoalkyl benzenes, dialkyl benzenes, olefin dimer, and olefin trimer.
[2]Estimated bromine index on a benzene-free and paraffin-free basis.

Example 6 shows the benefits of decreased bromine index and/or increased linearity that can be obtained when using the same catalyst in reactors 1 and 2. The operating conditions of D can be considered a "base case" in which reactors 1 and 2 are at the same temperature. The operating conditions of E have reactor 1 at a lower temperature and reactor 2 at a higher temperature than the operating conditions of D, so that reactor 2 is 45° F. (25° C.) hotter than reactor 1. The operating conditions of F have reactor 2 at yet a higher temperature, so that reactor 2 is 81° F. (45° C.) hotter than reactor 1. The operating conditions of G have reactor 1 at the same temperature as that in the operating conditions of D, while reactor 2 is at a temperature even higher than the operating conditions of F, so that reactor 2 is 90° F. (50° C.) hotter than reactor 1. A comparison of the results of D and E shows that for a constant bromine index of 140 linearity increased from 92.5 to 93.7 wt- %. A comparison of the results of D and F shows that for a constant linearity of between 92.5 and 92.7 wt- %, bromine index decreased from 140 to 100. However, a comparison of the results of D and G shows that linearity can decrease somewhat at high reactor 2 temperatures, but at the same time the bromine index decreased significantly.

Example 7

A sample of the catalyst prepared in Example 4 was loaded into a standard detergent alkylation pilot plant having a fixed bed reactor, which is referred to in this Example 7 as "reactor 1". The olefinic feed to reactor 1 was the same as that in Example 5, and the operating conditions of reactor 1 are shown in Table 8. The performance of an alumina-bound mordenite extrudate having a nominal 1/16 in (1.59 mm) diameter and a composition of 45 weight percent $SiO_2$ and 55 weight percent $Al_2O_3$ was evaluated in a standard detergent alkylation pilot plant with a fixed bed reactor, which is referred to in this Example 7 as "reactor 2." The feed to reactor 2 was the total alkylation reactor effluent of reactor 1, and the operating conditions of reactor 2 are shown in Table 8.

The results of H are comparative, because in H reactors 1 and 2 are at the same temperature while in J, K, and L the reactor 2 temperature is greater than the reactor 1 temperature.

In all of the operating conditions of Example 7, the reactor 2 catalyst volume is only about one-third of the catalyst volume of reactor 1.

TABLE 8

| Operating Conditions: | H | J | K | L |
|---|---|---|---|---|
| Reactor 1: | | | | |
| Pressure, psi(g) (kPa(g)) | 500 (3447) | 500 (3447) | 500 (3447) | 500 (3447) |
| LHSV, $hr^{-1}$ | 5.0 | 5.0 | 5.0 | 5.0 |
| Temperature, °F. (°C.) | 257 (125) | 266 (120) | 275 (135) | 275 (135) |
| Reactor 2: | | | | |
| Pressure, psi(g) (kPa(g)) | 500 (3447) | 500 (3447) | 500 (3447) | 500 (3447) |
| LHSV, $hr^{-1}$ | 15.0 | 15.0 | 15.0 | 15.0 |
| Temperature, °F. (°C.) | 257 (125) | 302 (150) | 347 (175) | 383 (195) |
| Reactor 2 Effluent: | | | | |
| Olefin Conversion, wt-% | ≅100 | ≅100 | ≅100 | ≅100 |
| Linearity, wt-% | 92.8 | 91.5 | 88.8 | 82.9 |
| Selectivities, wt-%: | | | | |
| LAB | 90.3 | 88.4 | 86.1 | 79.8 |
| Nonlinear alkyl benzene | 7.0 | 8.2 | 10.85 | 16.5 |
| $C_{20}$-plus heavies[1] | 2.7 | 3.4 | 3.05 | 3.7 |
| Bromine index[2] | 30 | 31 | 14 | 8 |

NOTES:
[1]$C_{20}$-plus heavies includes monoalkyl benzenes, dialkyl benzenes, olefin dimer, and olefin trimer.
[2]Estimated bromine index on a benzene-free and paraffin-free basis.

Example 7 shows that with a fluorided silica-alumina catalyst in the first reactor and an alumina-bound mordenite extrudate in the second reactor, although a temperature difference of 36° F. (20° C.) between reactors 1 and 2 (operating conditions J) did not yield a decrease in bromine index relative to the "base case" operating condition of H, further increases in the temperature difference to 72° F. (40° C.) at the operating condition of K and to 108° F. (60° C.) at the operating condition of L did yield significant decreases in the bromine index.

What is claimed is:

1. A process for producing an alkylaromatic comprising:
   a) passing a first feed stream comprising a feed olefin and a second feed stream comprising a feed aromatic to a first alkylation zone, reacting the feed olefin and the feed aromatic to form an alkylaromatic in the first alkylation zone in the presence of a first alkylation catalyst at first alkylation conditions, the first alkylation conditions comprising a first temperature, and withdrawing from the first alkylation zone an effluent stream comprising the alkylaromatic and a polymeric byproduct, wherein the effluent has an effluent linearity, and an effluent concentration of the polymeric byproduct;
   b) contacting at least a portion of the effluent stream comprising the alkylaromatic and the polymeric byproduct in a second alkylation zone with a second alkylation catalyst at second alkylation conditions, wherein the second alkylation conditions comprise a second temperature that is greater than the first temperature, producing a heavy alkylate in the second alkylation zone, and withdrawing from the second alkylation zone a polymer-depleted stream comprising the alkylaromatic and the heavy alkylate, wherein the polymer-depleted stream has a polymer-depleted linearity that is not greater than the effluent linearity, and a polymer-depleted concentration of the polymeric byproduct that is less than the effluent concentration;
   c) separating the polymer-depleted stream into a heavy alkylate stream enriched in the heavy alkylate and a product stream depleted in the heavy alkylate and containing a substantial portion of the alkylaromatic; and
   d) recovering the product stream from the process.

2. The process of claim 1 further characterized in that in the second alkylation zone the polymeric byproduct reacts with the alkylaromatic to produce the heavy alkylate.

3. The process of claim 1 further characterized in that a make-up stream comprising the feed aromatic is passed to the second alkylation zone, and in the second alkylation zone the feed aromatic reacts with the polymeric byproduct to produce the heavy alkylate.

4. The process of claim 1 further characterized in that the at least a portion of the effluent stream that is passed to the second alkylation zone comprises the feed aromatic, and in the second alkylation zone the feed aromatic reacts with the polymeric byproduct to produce the heavy alkylate.

5. The process of claim 1 further characterized in that the at least a portion of the effluent stream comprises an aliquot portion of the effluent stream.

6. The process of claim 1 wherein the first alkylation catalyst is a solid alkylation catalyst.

7. The process of claim 1 wherein the second alkylation catalyst is a solid alkylation catalyst.

8. The process of claim 1 further characterized in that the first alkylation catalyst is the same composition as the second alkylation catalyst.

9. The process of claim 1 further characterized in that the first alkylation catalyst and the second alkylation catalyst comprise silica-alumina.

10. The process of claim 1 further characterized in that the first alkylation catalyst and the second alkylation catalyst comprise fluorided silica-alumina.

11. The process of claim 1 further characterized in that the polymeric byproduct comprises a dimer of the feed olefin.

12. The process of claim 1 further characterized in that the separating of the polymer-depleted stream in Step (c) comprises fractionating the polymer-depleted stream.

13. The process of claim 1 further characterized in that the effluent stream has an effluent bromine index in the range of from about 240/MW to about 1200000/MW, where the effluent bromine index is measured by UOP Method 304-90 and is on a feed-aromatic-free and paraffin-free basis and MW is the average molecular weight of the alkylaromatics in the effluent stream.

14. The process of claim 1 further characterized in that the polymer-depleted stream has a polymer-depleted bromine index of less than 240000/MW, where the effluent bromine index is measured by UOP Method 304-90 and is on a feed-aromatic-free and paraffin-free basis and MW is the average molecular weight of the alkylaromatics in the polymer-depleted stream.

15. The process of claim 1 further characterized in that the effluent stream has an effluent bromine index and the polymer-depleted stream has a polymer-depleted bromine index that is less than the effluent bromine index, where the effluent bromine index and the polymer-depleted bromine index are measured by UOP Method 304-90 and are computed on an feed-aromatic-free and paraffin-free basis.

16. The process of claim 1 further characterized in that the feed olefin comprises an olefinic hydrocarbon having from 10 to 22 carbon atoms.

17. The process of claim 1 further characterized in that the feed aromatic comprises a compound selected from the group consisting of benzene and alkylated derivatives of benzene.

18. The process of claim 1 further characterized in that the effluent stream has a molar ratio of the feed olefins per the alkylaromatic of less than 0.1:1.

19. The process of claim 1 further characterized in that the effluent stream has a molar ratio of the polymeric byproduct per the alkylaromatic of less than 0.05:1.

20. The process of claim 1 wherein the effluent linearity is greater than 85 %.

21. The process of claim 20 wherein the effluent linearity is greater than 90%.

22. The process of claim 1 wherein the second temperature is at least 9° F. greater than the first temperature.

23. The process of claim 22 wherein the second temperature is at least 36° F. greater than the first temperature.

24. The process of claim 1 wherein the second temperature is greater than the first temperature and up to 90° F. greater than the first temperature.

25. The process of claim 1 further characterized in that the first alkylation conditions comprise a first liquid hourly space velocity of between about 0.5 and about 20 $hr^{-1}$ and the second alkylation conditions comprise a second liquid hourly space velocity of between about 10 and about 30 $hr^{-1}$.

26. The process of claim 1 further characterized in that a makeup stream comprising the feed olefins is not introduced to the second alkylation zone.

27. The process of claim 1 further characterized in that the first temperature comprises the highest temperature in the first alkylation zone and the second temperature comprises the lowest temperature in the second alkylation zone.

* * * * *